United States Patent [19]

Nouws et al.

[11] Patent Number: 5,021,594
[45] Date of Patent: Jun. 4, 1991

[54] ENHANCED REDUCTION AND INHIBITION OF ETU CONTENT IN ALKYLENEBISDITHIOCARBAMATES

[75] Inventors: Jacobus A. M. Nouws, Etten-leur; Pieter Kool, Oostvoorne; Pieter C. Diepenhorst, Spijkenisse, all of Netherlands

[73] Assignee: Pennwalt France S.A., Plaisir, France

[21] Appl. No.: 492,526

[22] Filed: Mar. 12, 1990

[51] Int. Cl.$^5$ .................. C07C 155/06; C07F 13/00
[52] U.S. Cl. ........................................ 556/38; 556/2; 556/37; 556/45; 556/130; 556/134; 556/146
[58] Field of Search ............... 556/2, 37, 38, 45, 118, 556/130, 134, 138, 146; 514/1, 6, 184, 492, 494, 499, 500, 501, 579, 580

[56] References Cited

U.S. PATENT DOCUMENTS

| | | |
|---|---|---|
| 3,004,002 | 10/1961 | Kaplan et al. . |
| 3,210,394 | 10/1965 | Nemec et al. . |
| 3,379,610 | 4/1968 | Lyon et al. . |
| 3,869,486 | 3/1975 | Van den Boogaart et al. . |
| 4,079,146 | 3/1978 | Miller et al. ............ 556/39 X |
| 4,185,113 | 1/1980 | Virrion et al. ............ 556/39 X |
| 4,203,999 | 5/1980 | Martin et al. ............ 556/39 X |
| 4,217,293 | 8/1980 | Adams, Jr. . |
| 4,315,846 | 2/1982 | Kuchikata et al. ............ 556/39 X |
| 4,344,890 | 8/1982 | Adams, Jr. . |
| 4,390,705 | 6/1983 | Gozzo et al. ............ 556/39 X |

FOREIGN PATENT DOCUMENTS 890669 2/1982 Belgium .
0008533 3/1980 European Pat. Off. .

Primary Examiner—Arthur C. Prescott
Attorney, Agent, or Firm—Panitch Schwarze Jacobs & Nadel

[57] ABSTRACT

A method is provided for stabilizing alkylenebisdithiocarbamates, such as 1,2-ethylenebisdithiocarbamates, (EBDC) by mixing the EBDC with formaldehyde or formaldehyde releasing agents (donor) and a co-polymerization agent which forces the polymerization reaction of formaldehyde and ethylenethioureas toward completion to reduce and stabilize the content of and inhibit the formation of ethylenethiourea (ETU) in the EBDC. Paraformaldehyde as donor is preferably added in an amount of about 0.1 to 2 weight percent based upon the EBDC, together with a co-polymerization agent such as melamine or hydroquinone. The stabilized EBDC product contains aldehyde, co-polymerization agent, mono- and /or dimethylolethylenethioureas and polymerization products thereof, and less than about 0.015 weight percent ETU per se.

18 Claims, No Drawings

5,021,594

ENHANCED REDUCTION AND INHIBITION OF ETU CONTENT IN ALKYLENEBISDITHIOCARBAMATES

FIELD OF THE INVENTION

The present invention relates to the reduction and inhibition of ethylenethiourea (ETU) in alkylenebisdithiocarbamates. More particularly, the invention is directed to a method of inhibiting the formation of and reducing the ETU content and stabilizing the ETU content at very low levels, preferably less than 0.015 weight percent, in alkylenebisdithiocarbamate formulations.

BACKGROUND OF THE INVENTION

Various salts of 1,2-ethylenebisdithiocarbamic acid have been known for many years as agents for combating plant diseases caused by fungi. Among the ethylenebisdithiocarbamates (sometimes referred to as "EBDC") useful as plant fungicides are the manganese, zinc, nickel, cobalt, copper, sodium, potassium and ammonium salts of 1,2-ethylenebisdithiocarbamic acid or co-reacted metal EBDC. Preferred fungicides of this class are manganese EBDC (maneb), zinc EBDC (zineb), and particularly zinc coordination complexes of manganese EBDC (mancozeb).

A problem with the EBDCs is that they tend to degrade over time due to factors including oxidation, heat, humidity, etc., into, among other things, ethylenethiourea (2-imidazolidinethion), commonly known as ETU. Due to this degradation, ETU content increases in concentration during storage of the EBDC. Since ETU has been found to have carcinogenic and teratogenic effects in laboratory animals, and no significant biological activity as a fungicide has been observed, ETU is an unwanted degradation product.

Over the years a number of processes and additives have been developed to reduce the ETU content of EBDCs. It is desirable that the ETU content of EBDC formulations be reduced to less than 0.015 percent by weight, based on the weight of the EBDC in the formulation. Several prior attempts have been made to reduce the content of ETU in EBDC by adding formaldehyde or formaldehyde precursor (formaldehyde donor) to the aqueous reaction mixture, preferably with a water-soluble zinc salt, and also by optionally adding paraformaldehyde or another formaldehyde releasing agent (precursor or generator) to the dried product. See, for example, U.S. Pat. Nos. 4,217,293 and 4,344,890 of Adams. However, processes of even further reducing ETU content in EBDC are desired.

SUMMARY OF THE INVENTION

According to the present invention, a method is provided for stabilizing alkylenebisdithiocarbamates by mixing with the EBDC an amount of a formaldehyde donor effective to reduce the content of ethylenethiourea in the EBDC and an amount of co-polymerization agent (crosslinker) effective to force the polymerization reactions of formaldehyde and ethylenethioureas toward termination. The formaldehyde donor is preferably mixed in an amount of about 0.1 to 2 weight percent based on the weight of EBDC. Preferably, paraformaldehyde and a crosslinker, such as hydroquinone or melamine, are mixed with the EBDC in either a dry or wet state. The stabilized product contains residual aldehyde and crosslinker, (di)methylolethylenethioureas and polymerization products thereof, and less than about 0.015 weight percent ethylenethiourea per se based on the weight of EBDC.

DETAILED DESCRIPTION OF PREFERRED EMBODIMENTS

Fungicidal salts of 1,2-ethylenebisdithiocarbamic acid are well known in the art and commercially available from a number of agricultural chemical companies, including Atochem North America, Inc. (formerly Pennwalt Corporation), Rohm & Haas Company, E.I. duPont de Nemours & Company, Roussel UCLAF, etc. Particularly preferred are the zinc and manganese coordination complexes of EBDC (mancozeb) which may be made by various processes, such as those described in U.S. Pat. Nos. 3,210,394; 3,379,610 and 3,869,486.

These fungicides are available in various forms, including aqueous liquid formulations and dry wettable powders ("WP"). An example of one commercially available fungicide of this type is "PENNCOZEB" fungicide, which is a product available from Atochem North America, Inc. containing 80 percent active ingredient of a coordination product of maneb and a zinc salt consisting of 16 percent manganese ions, 2 percent zinc ions, 62 percent ethylenebisdithiocarbamate ($C_4H_6N_2S_4$) ions and 20 percent inert ingredients.

However, it will be understood that the present invention is applicable to any alkylenebisdithiocarbamate, particularly alkylene-1,2-bis-dithiocarbamates, which contains or yields ethylenethiourea (ETU) or ETU-like products as a degradation product. Other such alkylenebisdithiocarbamates, which can be considered as homologues of ethylenebisdithiocarbamates, include propineb (zinc 1-methyl-1,2-ethylenebisdithiocarbamate) which produces methyl-ETU, and metiram (zineb-ethylene thiuram disulfide adduct). For ease of reference herein, all of the alkylenebisdithiocarbamates and homologues which contain or yield ETUs will be referred to as "EBDCs."

The present invention is based upon the known reaction of ETU with formaldehyde directly or from paraformaldehyde or any other formaldehyde donor (precursor), all of which will be referred to generally herein as "formaldehyde donors." When about 0.3 to 1 weight percent formaldehyde or paraformaldehyde is added to mancozeb (e.g., PENNCOZEB WP), the ETU content slowly decreases to a level of about 0.02 weight percent based on the EBDC. This decrease is due to the reaction of ETU with formaldehyde donor to yield mono- and/or dimethylolethylenethioureas, which in turn tend to polymerize. These reactions are reversible, so that a large amount of formaldehyde donor is needed to achieve a low ETU content.

To achieve a reaction equilibrium with lower ETU content, it has been found according to the present invention that certain copolymerization agents can be added to the EBDC system together with a formaldehyde donor to cause a shift of the equilibrium of the polymerization reactions in the direction of completion, so that more ETU will react and remain bonded in the polymeric form. The co-polymerization agents which have been found to be effective according to the present invention are generally those which show the same kind of polymerization reactions with formaldehyde (i.e., addition to formaldehyde followed by condensation).

Suitable co-polymerization agents (crosslinkers) include, for example, nucleophilic active aromatic compounds such as hydroquinone, melamine, benzoquinone, methoxyhydroquinone, 1,2-naphthoquinone, 1,4-naphthoquinone, pyrocatechol, resorcinol, phloroglucinol dihydrate, γ-pyran; melamine and N-mono- and N,N'-disubstituted melamines such as N-butylmelamine, N,N'-dibutylmelamine; and 2,4-diamino-1,3,5-triazines such as 2,4-diamino-6-chloro-1,3,5-triazine, 2-phenoxy-4,6-diamino-1,3,5-triazine, ammeline and ammelide. Of these, melamine and hydroquinone are preferred.

Suitable formaldehyde donors include, for example, paraformaldehyde, hexamethylene tetramine (hexamine), Z-1-(chloroallyl)-3,5,7-triaza-1-azonia-adamantane chloride (Dowicil 200), imidazolidinyl urea (Germall 115), 1,3,5-triazine-1,3,5-(2H,4H,6H) triethanol (Grotan BK), benzylalcohol mono (poly) hemiformal (Preventol D ), sodium hydroxymethane sulphonate. PENNCOZEB formulations always contain 1–3% hexamine as thermal stabilizer.

The amount of crosslinker which will be effective to force the equilibrium of the polymerization reaction in the direction of completion (termination) will vary somewhat due to the particular co-polymerization compound, due in part to the number of sites available for reaction with formaldehyde. For example, about 0.02 to 0.25 weight percent melamine or 0.05 to 0.5 percent hydroquinone, based upon the weight of the EBDC, has been found satisfactory to enhance the reduction of ETU from that normally obtained by the addition of formaldehyde or paraformaldehyde alone. When the aldehyde and crosslinker are added to the EBDC in the dry state and mixed by milling, slightly higher amounts of the crosslinker, such as 0.02 to 0.5 weight percent melamine or 0.05 to 1 weight percent hydroquinone, are preferable in order to account for possibly less complete dispersion in the dry mixture as compared to the mixing in an aqueous medium.

Similarly, with the use of a copolymerization agent according to the present invention, the amount of aldehyde required for the reduction of the ETU content is smaller than when formaldehyde or paraformaldehyde is added alone (e.g., 2 to 5 weight percent paraformaldehyde is normally used). Accordingly, the formaldehyde donor may be added in amounts of about 0.1 to 2, and preferably 0.3 to 1 weight percent based on the weight of the EBDC.

The formaldehyde donor and copolymerization agent (crosslinker) may be mixed with the EBDC in any of a number of ways, including, for example:

(1) formaldehyde donor and crosslinker may be added to an aqueous formulation or to the undried EBDC product, which is generally a moist granular paste (about 25 percent water) obtained from the reaction mixture for forming the EBDC;

(2) formaldehyde donor and crosslinker may be added with water to the dried EBDC;

(3) formaldehyde donor and crosslinker may be added to the dried EBDC and mixed intensly, such as by milling. Other possibilites will be evident to those skilled in the art based upon the present disclosure.

Where an aqueous medium is used, the amount of water which is present in the mixture is that amount which is sufficient to allow good dispersion of the formaldehyde donor and crosslinker throughout the EBDC formulation so that it will be available for further reaction with ETU during storage. It is preferred that the reaction mixture contains at least two hundred percent water by weight based upon the weight of the dry EBDC. This is sufficient to form an aqueous paste or thick slurry of the EBDC.

The reaction parameters for the present invention are not particularly critical. Mixing may suitably be carried out in about 5 minutes at room temperature, but other times, temperatures and water contents may be used, as will be appreciated by one skilled in the art. It is only necessary that the conditions be such as to obtain homogeneous distribution of the reactants with the EBDC particles. The stabilizing reaction will thereafter take place, directly, during drying and storage.

The aqueous medium need only remain for sufficient time to obtain good dispersion of the formaldehyde donor and crosslinker with the EBDC. Thereafter, the mixture is dried, preferably under vacuum, to a powder. It is also possible to leave the EBDC undried as an aqueous formulation. In either event, oxygen and high temperatures should be avoided during drying and storage due to their degradative effects on the EBDC.

A preferred method which does not require the addition of water or the use of an aqueous medium is to mix the formaldehyde donor and crosslinker with the EBDC in its dried state using intense mixing, such as milling. Paraformaldehyde is much more easily added to the dried EBDC than formaldehyde solution. Paraformaldehyde is further advantageous over the formaldehyde solution in that paraformaldehyde slowly disintegrates into formaldehyde, and there is therefore a longer period of time that formaldehyde will be available for reaction with ETU in this manner.

The method of the present invention may be illustrated by the following reaction equations. The paraformaldehyde degrades to formaldehyde according to the equilibrium reaction shown in equation I below:

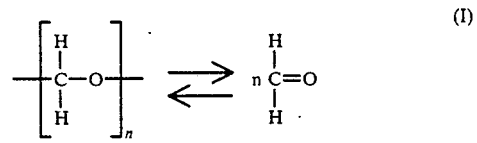

(I)

Reactions of formaldehyde with ETU are well known and are described, for example, in Kaplan et al. U.S. Pat. No. 3,004,002. These reactions include the formation of mono- and/or dimethylolethylenethioureas, namely, N-methylolethylenethiourea and N,N'-dimethylolethylenethiourea, as shown in equation II below:

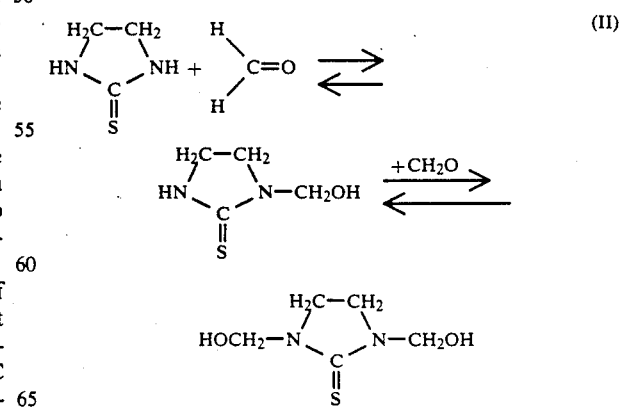

(II)

These reaction products have a strong tendency to polymerize and will, depending upon circumstances and concentrations, yield the reactions shown in equations III and IV below:

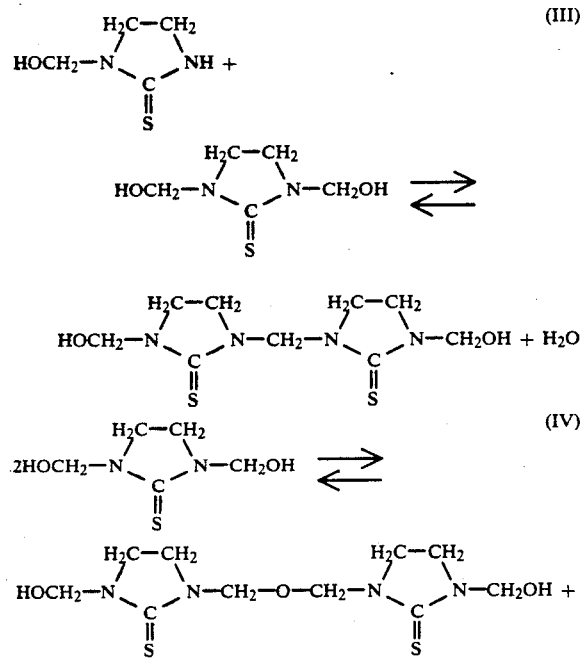

As indicated above, reactions III and IV are reversible, and the addition of a co-polymerization agent results in a shift of the equilibrium toward the direction of completion so that more ETU will react and remain bonded to the polymer. The reactions of formaldehyde with melamine and hydroquinone are shown in equastions V and VI below:

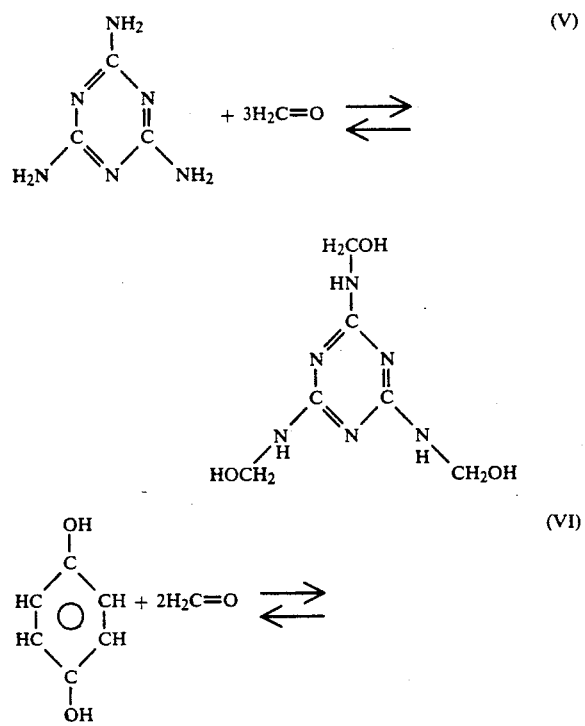

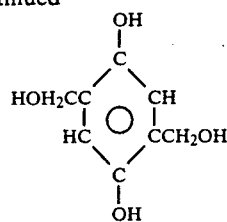

These reaction products then participate in polymerization reactions similar to equations III and IV, as shown in equations VII and VIII below (wherein X is a reaction product of formaldehyde and co-polymerization agent, such as shown in equations V and VI above):

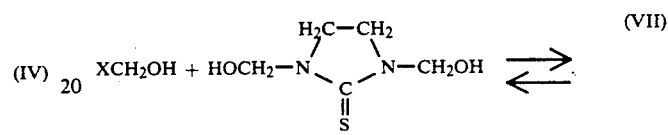

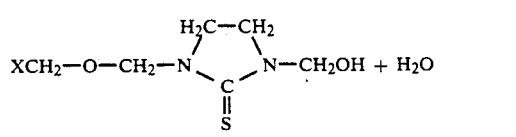

It will be understood that the reaction products of equations VII and VIII above can form further condensation products to bigger molecules.

The excess formaldehyde donor and copolymerization agent acts as a stabilizer for the ethylenethiourea content on degradation of the EBDC during storage. As a result, the stabilized EBDCs according to the present invention will contain unreacted or residual aldehyde and co-polymerization agent, mono- and/or dimethylolethylenethioureas and polymerization products thereof, and less than about 0.015 weight percent ethylenethiourea (ETU) per se based o the weight of the EBDC.

Without co-polymerization agents, the lowest ETU levels reached by the reaction of equation (II) above were about 0.02 weight percent. Using the co-polymerization agents according to the present invention the ETU content can be easily reduced by another factor of 2 (i.e., to about 50% of the levels obtained using formaldehyde donor alone). Moreover, when the co-polymerization agents of the present invention are added in combination with a formaldehyde donor, the resulting product stays at a lower ETU content for a longer period of time than products without the copolymerization agent addition. EBDCs treated according to the present invention have remained stabilized for at least 2½ years.

In addition, hydroquinone crosslinkers have the advantage that they are also reducing agents which partly prevent or inhibit the formation of additional ETU via oxidative decomposition. Where paraformaldehyde is used instead of formaldehyde, the slow disintegration makes formaldehyde available for a longer period of time for reaction with the ETU and co-polymerization agent.

The present invention will now be illustrated with further reference to the following specific, non-limiting examples:

EXAMPLE 1

To 600 grams of undried PENNCOZEB (technical or formulation) were added 0.39 weight percent formaldehyde and 0.46 weight percent hydroquinone. After 5 minutes, the wet paste was dried in a vacuum 10 mm Hg for 960 minutes at 20° C.) to a water content of 0.6%. The same treatment was done without copolymerization agent and without either aldehyde or co-polymerization agent. For the fully-treated product, the ETU content was 0.022 weight percent immediately after drying; for the product without hydroquinone, the ETU content was 0.049 weight percent immediately after drying; and for the product without addition of either formaldehyde or hydroquinone, the ETU content was 0.068 weight percent immediately after drying.

EXAMPLE 2

The same mixtures were prepared as in Example 1, but the mixture was freeze dried to a water content of 2.6%. Immediately after drying, the ETU content was 0.014 weight percent, which increased to 0.021 weight percent after 25 days. Without the addition of hydroquinone, the ETU content was immediately 0.016 weight percent, and 0.054 weight percent after 18 days. For the product without either formaldehyde or hydroquinone, the ETU content was 0.114 weight percent immediately, and 0.142 weight percent after 28 days.

EXAMPLE 3

To 4 grams of PENNCOZEB WP, initially containing 0.05 weight percent of ETU, Were added 12 milligrams paraformaldehyde, 2 milligrams melamine and 10 ml water. After 5 minutes, the wet paste was dried in a vacuum (10 mm Hg for 960 minutes at 70° C.) to a water content of 0.7%. Within 15 days, an ETU content of 0.006 weight percent was reached and remained stable for at least 1.5 years stored at room temperature.

In contrast, the same product without the addition of melamine reached an ETU content of 0.012 weight percent in 15 days and remained stable for only 20 days (increasing thereafter to 0.017% and staying on that level (0.017%) for at least 1.5 years).

EXAMPLE 4

To 4 grams of PENNCOZEB WP, initially containing 0.05 weight percent of ETU, were added 12 milligrams paraformaldehyde, 2 milligrams hydroquinone and 10 ml water. After 5 minutes, the wet paste was dried in a vacuum (10 mm Hg for 960 minutes at 70.C) to a water content of 0.5% Within 15 days, an ETU content of 0.007 weight percent was reached and remained stable for at least 75 days stored at room temperature.

In contrast, the same product without the addition of hydroquinone reached an ETU content of 2 weight percent in 15 days and remained stable for only 20 days (increasing thereafter to 0.017% and staying on that level (0.016%) for at least 75 days).

EXAMPLE 5

To 50 grams of PENNCOZEB WP, having an initial ETU content of 0.07 weight percent, were added 80 milligrams paraformaldehyde and 260 milligrams hydroquinone. The ingredients were mixed by milling. Within 25 days, an ETU content of 0.014 weight percent was reached and remained stable for at least days stored at room temperature.

In contrast, the same product made without hydroquinone reached an ETU content of 0.038 weight percent and remained stable at that level for 80 days.

EXAMPLE 6

To 700 grams of the undried PENNCOZEB (technical) were added 0.1 weight percent formaldehyde, 0.18 weight percent hydroquinone and 0.4 weight percent paraformaldehyde. After mixing for 5 minutes, the wet paste was dried in a vacuum (10 mm Hg for 960 minutes at 70° C.) to a water content of 0.8%. The same treatment was done without formaldehyde, paraformaldehyde, and co-polymerization agent.

For the completely formulated water dispersable powder, the ETU content was 0.023 weight percent directly, 0.010 weight percent after 21 days, and stayed stable for at least 2.5 years (0.012 weight percent); and for the product without addition of formaldehyde, paraformaldehyde and hydroquinone, the ETU content was 0.056 weight percent directly, 0.050 weight percent after 21 days, and 0.052 weight percent after 2.5 years.

EXAMPLE 7

To 700 grams of undried PENNCOZEB (technical) were added 0.1 weight percent formaldehyde, 0.4 weight percent paraformaldehyde and 0.23 weight percent malamine. After mixing for 5 minutes, the wet paste was dried in a vacuum (10 mm Hg for 960 minutes at 70° C.) to a water content of 0.7 weight percent (I). The same treatment was done with 0.07 weight percent melamine (II) and without formaldehyde, paraformaldehyde, and co-polymerization agent (III).

For the above-formulated water dispersable powders, the ETU contents are found in table I below.

TABLE I

| | ETU Concentrations in PENNCOZEB | | |
| --- | --- | --- | --- |
| | ETU Weight Percent | | |
| Product | Directly | After 8 Days | After 2.5 Years |
| I | 0.058 | 0.015 | 0.013 |
| II | 0.065 | 0.011 | 0.014 |
| III | 0.057 | 0.045 | 0.054 |

The present invention may be embodied in other specific forms without departing from the spirit or essential attributes thereof and, accordingly, reference should be made to the appended claims, rather than to the foregoing specification as indicating the scope of the invention.

We claim:

1. A method of stabilizing alkylene dithiocarbamates (EBDC) comprising mixing with the EBDC a formaldehyde donor and a co-polymerization agent for formaldehyde, which co-polymerization agent forces the polymerization reaction of formaldehyde and ethylenethioureas toward completion, said formaldehyde donor and copolymerization agent being mixed with the EBDC in amounts effective to reduce the content of ethylenethiourea in the EBDC.

2. A method according to claim 1 wherein said formaldehyde donor is selected from the group consisting of formaldehyde and paraformaldehyde.

3. A method according to claim 1 wherein said EBDC is a salt of 1,2-ethylenebisdithiocarbamate.

4. A method according to claim 3 wherein the cation of the EBDC is selected from the group consisting of manganese, zinc, nickel, cobalt, copper, sodium, potassium, ammonium and co-reacted complexes thereof.

5. A method according to claim 4 wherein the EBDC is a co-reacted complex with manganese and zinc.

6. A method according to claim 1 wherein the formaldehyde donor is mixed in an amount of about 0.1 to 2 weight percent based on the EDBC.

7. A method according to claim 1 wherein the formaldehyde donor is mixed with an undried EBDC.

8. A method according to claim 1 wherein water and formaldehyde donor are mixed with the EBDC.

9. A method according to claim 8 wherein water is mixed in an amount of at least 200 weight percent based on the EBDC.

10. A method according to claim 1 wherein the formaldehyde donor is mixed with an aqueous formulation of the EBDC.

11. A method according to claim 1 wherein the mixture is subsequen-tly dried to a powder.

12. A method according to claim 11 wherein the mixture is vacuum dried.

13. A method according to claim 1 wherein the formaldehyde donor is paraformaldehyde which is mixed with dried EBDC by milling.

14. A method according to claim 1 wherein the formaldehyde donor is selected from the group consisting of hexamethylene tetramine, Z-1-(chloroallyl)-3,5,7-triaza-1-azonia-adamantane chloride, imidazolidinyl urea, 1,3,5-triazine-1,3,5-(2H,4H,6H) triethanol, benzylalcohol mono (poly) hemiformal, and sodium hydroxymethane sulphonate.

15. A method according to claim 1 wherein the co-polymerization agent is selected from the group consisting of hydroquinone, melamine, benzoquinone, methoxyhydroquinone, 1,2-naphthoquinone, 1,4-naphthoquinone, pyrocatechol, resorcinol, phloroglucinol dihydrate and γ-pyran.

16. A method according to claim 15 wherein the co-polymerization agent comprises melamine which is mixed in an amount of about 0.02 to 0.5 weight percent based on the EBDC.

17. A method according to claim 15 wherein the co-polymerization agent comprises hydroquinone which is mixed in an amount of about 0.05 to 1.0 weight percent based on the EBDC.

18. A stabilized 1,2-ethylenebisdithiocarbamate containing formaldehyde, a copolymerization agent selected from the group consisting of hydroquinone and melamine, monoand/or dimethylolethylenethiourea and polymerization products thereof, and less than about 0.015 weight percent ethylenethiourea per se based on the weight percent of the ethylenebisdithiocarbamate.